United States Patent
Zanghellini

(10) Patent No.: US 9,523,105 B2
(45) Date of Patent: Dec. 20, 2016

(54) FERMENTATION ROUTE FOR THE PRODUCTION OF LEVULINIC ACID, LEVULINATE ESTERS AND VALEROLACTONE AND DERIVATIVES THEREOF

(75) Inventor: Alexandre Luc Zanghellini, Seattle, WA (US)

(73) Assignee: ARZEDA CORPORATION, Seattle, WA (US)

( * ) Notice: Subject to any disclaimer, the term of this patent is extended or adjusted under 35 U.S.C. 154(b) by 571 days.

(21) Appl. No.: 13/820,028

(22) PCT Filed: Aug. 30, 2011

(86) PCT No.: PCT/US2011/049788
§ 371 (c)(1),
(2), (4) Date: Aug. 22, 2013

(87) PCT Pub. No.: WO2012/030860
PCT Pub. Date: Mar. 8, 2012

(65) Prior Publication Data
US 2013/0330779 A1    Dec. 12, 2013

Related U.S. Application Data

(60) Provisional application No. 61/378,199, filed on Aug. 30, 2010.

(51) Int. Cl.
| | | |
|---|---|---|
| *C12P 7/62* | (2006.01) | |
| *C12P 7/40* | (2006.01) | |
| *C12P 7/42* | (2006.01) | |
| *C12P 17/04* | (2006.01) | |

(52) U.S. Cl.
CPC .. *C12P 7/62* (2013.01); *C12P 7/40* (2013.01); *C12P 7/42* (2013.01); *C12P 17/04* (2013.01); *C12Y 101/01* (2013.01); *C12Y 401/03016* (2013.01); *C12Y 401/03039* (2013.01); *C12P 2203/00* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,769,929 | A | 6/1998 | Gundlach et al. |
| 6,965,058 | B1 | 11/2005 | Raidel et al. |
| 7,153,996 | B2 * | 12/2006 | Fagan ............... C07C 67/04 560/174 |
| 2008/0242721 | A1 | 10/2008 | Selifonov |
| 2009/0191607 | A1 | 7/2009 | Baker et al. |

FOREIGN PATENT DOCUMENTS

| | | |
|---|---|---|
| CN | 1643116 A | 7/2005 |
| EP | 0496555 A2 | 7/1992 |
| EP | 0882745 A1 | 12/1998 |
| EP | 1533364 A2 | 5/2005 |
| EP | 1716131 B1 | 11/2006 |
| JP | H 05320023 A | 12/1993 |
| JP | H 06280041 A | 10/1994 |
| JP | H 09190820 A | 7/1997 |
| JP | 2009528842 A | 8/2009 |
| WO | WO 95/22524 A1 | 8/1995 |
| WO | WO 98/43684 A1 | 10/1998 |
| WO | WO 2004/084633 A1 | 10/2004 |
| WO | WO 2004/085048 A2 | 10/2004 |
| WO | WO 2004/085349 A2 | 10/2004 |
| WO | WO 2004/085390 A1 | 10/2004 |
| WO | WO 2005/028529 A2 | 3/2005 |
| WO | WO 2005/063726 A1 | 7/2005 |
| WO | WO 2005/097723 A2 | 10/2005 |
| WO | WO 2006/015023 A2 | 2/2006 |
| WO | WO 2006/015024 A1 | 2/2006 |
| WO | WO 2006/117113 A2 | 11/2006 |
| WO | WO 2007/106524 A2 | 9/2007 |
| WO | WO 2009/142489 A2 | 11/2009 |
| WO | WO 2010/051076 A1 | 5/2010 |
| WO | WO 2010/065833 A2 | 6/2010 |
| WO | WO 2010/077470 A2 | 7/2010 |
| WO | WO 2011/066076 A1 | 6/2011 |

OTHER PUBLICATIONS

Ezeji et al., Bioproduction of butanol from biomass: from genes to bioreactors, Current Opinion in Biotechnology 2007, 18:220-227.*
Geary et al., The state of the art in asymmetric induction: the aldol reaction as a case study, Tetrahedron: Asymmetry 20 (2009) 131-173.*
Evans et al., C2-Symmetric Copper (II) Complexes as Chiral Lewis Acids. Scope and Mechanism of the Catalytic Enantioselective Aldol Additions of Enolsilanes to Pyruvate Esters, J. Am. Chem. Soc. 1999, 121, 686-699.*
Blackwell, N.C., "Mechanistic and Structural Investigations of DDG Aldolase," a thesis submitted for the degree of Doctor of Philosophy at the University of Leicester, Oct. 2000.
Bozell, J., "Connecting Biomass and petroleum processing with a chemical bridge", *Science*, 329: 522-523 (2010).
Bozell, J., "Production of levulinic acid and use as a platform chemical for derived products", *Resources, Conservation and Recycling*, 28: 227-239 (2000).
Ezeji, T.C. et al., "Bioproduction of butanol from biomass: from genes to bioreactors", *Current Opinion in Biotechnology*, 18(3): 220-227 (2007).
Ishiyama et al., "Structural studies of FlaA1 from helicobacter pylori reveal the mechanism for inverting 4,6-dehydratase activity", *J. Bio. Chem.*, 281(34): 24489-24495 (2006).
Li, Y., et al., "Biotechnological production of pyruvic acid", *Applied Microbiology and Biotechnology*, 57: 451-459 (2001).

(Continued)

*Primary Examiner* — Suzanne M Noakes
*Assistant Examiner* — Stephen Chong
(74) *Attorney, Agent, or Firm* — Cooley LLP

(57) ABSTRACT

The invention provides processes for the conversion of pyruvate obtained from sugars or other carbon sources, to valuable C5 materials such as levulinic acid, levulinate esters, valerolactone, and derivatives thereof.

28 Claims, 9 Drawing Sheets

(56) References Cited

OTHER PUBLICATIONS

Lüönd, R.M., et al., "Assessment of the active-site requirements of 5-aminolaevulinic acid dehydratase: Evaluation of substrate and product analogues as competitive inhibitors", *J. Org. Chem.*, 57(18): 5005-5013 (1992).

Martin, C.H., et al., "Integrated bioprocessing for pH-dependent of 4-valerolactone from levulinate in Pseudomonas Putida KT2440", *App. and Environ, Microbiology*, 76(2): 417-424 (2010).

Martin, C.H. et al., "High-titer production of monomeric hydroxyvalerates from levulinic acid in Pseudomonas putida", *Journal of Biotechnology*, 139(1): 61-67 (2009).

Meyers et al., "Stereoselective alkylations in rigid systems. Effect of remote substituents on p-facial additions to lactam enolates. Stereoelectronic and steric effects", *J. Am. Chem. Soc.*, 120(30): 7429-7438 (1998).

PCT/US2011/049788, International Search Report and Written Opinion, mailed Jan. 19, 2012, 10 pages.

PCT/US2011/049788, International Preliminary Report on Patentability, mailed Mar. 5, 2013, 5 pages.

Pollard, J. R. et al., "Substrate selectivity and biochemical properties of 4-hydroxy-2-keto-pentanoic acid aldolase from *Escherichia coli*", *Applied and Environmental Microbiology*, 64(10): 4093-4094 (1998).

Serrano-Ruiz et al., "Catalytic upgrading of levulinic acid to 5-nonanone", *Green Chemistry*, 12(4): 574-577 (2010).

Stuermer et al., "Asymmetric bioreduction of activated C=C bonds using enoate reductases from the old yellow enzyme family", *Current Opinion in Chemical Biology*, 11(2): 203-213 (2007).

Wang, W., et al., "Comparison of two metal-dependent pyruvate aldolases related by convergent evolution: substrate specificity, kinetic mechanism, and substrate channeling", *Biochemistry*, 49: 3774-3782 (2010).

Wang and Seah, "Purification and biochemical characterization of a pyruvate-specific Class II aldolase, Hpal", *Biochemistry*, 44(27): 9447-9455 (2005).

Zanghellini, A. et al., "New algorithms and an in silico benchmark for computational enzyme design", *Protein Science*, 15(12): 2785-2794 (2006).

Bur et al., "An evaluation of the substrate specificity and asymmetric synthesis potential of the cloned L-lactate dehydrogenase from *Bacillus stearothermophilus,*" *Canadian Journal of Chemistry* 67: 1065-1070, 1989.

\* cited by examiner

FERMENTATION ROUTE FOR THE PRODUCTION OF LEVULINIC ACID, LEVULINATE ESTERS AND VALEROLACTONE AND DERIVATIVES THEREOF

PRIORITY

This application claims priority to U.S. Provisional Application No. 61/378,199, filed Aug. 30, 2010, which is hereby incorporated by reference.

BACKGROUND

Levulinic acid, or 4-oxopentanoic acid, is an organic compound with the formula $CH_3C(O)CH_2CH_2CO_2H$. It is a keto acid. Levulinic acid is typically prepared chemically, for example, by heating sucrose with concentrated hydrochloric acid. The process proceeds via the intermediacy of glucose, which is isomerized to fructose and then hydroxymethylfurfural.

Levulinic acid is a potential precursor to nylon-like polymers, synthetic rubbers, and plastics. Levulinic acid is a versatile synthetic intermediate, e.g., in the synthesis of pharmaceuticals, and is a precursor in the industrial production of other chemical commodities such as methyltetrahydrofuran, valerolactone, and ethyl levulinate.

SUMMARY OF THE INVENTION

In certain aspects and embodiments, the invention provides a chemical pathway for the conversion of pyruvate obtained from sugars or other carbon sources, to valuable C5 materials such as levulinic acid. Exemplary C5 compounds are shown in FIGS. 1 and 2. When used with sugars as a carbon source, the key to the pathway is to convert C6 sugars (such as, but not limited to, glucose, fructose, galactose) and/or C5 sugars (such as, but not limited to, xylose, arabinose) into pyruvate, and subsequently convert pyruvate into one or several valuable C5 compounds through chemical or biochemical aldol addition, oxidation, reduction, dehydration and cyclization reactions. When used with another carbon source such as, but not limited to, fatty acids and glycerol, the carbon source is first converted into pyruvate, and subsequently converted to one or several valuable C5 compounds, which include linear C5 keto acids or esters or cyclized derivatives thereof of the following general formula: $C_5C_4(X)C_3C_2(Y)C_1(=O)(Z)$, where X is either a hydroxyl or ketone oxygen, Y is either a hydrogen, a hydroxyl or ketone oxygen, the bond between the C3 and C2 carbons is either single of double (e.g. saturated or unsaturated) and Z is an alkoxy, sulfide or phenoxy group as to make either an ester, thioester or carboxylic acid functional group. In some embodiments, the C5 compound is $C_5C_4(O_1)C_3C_2(Y)C_1(=O)(O_1)$, wherein the indice "$O_1$" denotes the same oxygen atom such that there is a cyclic ester, or lactone formed, and Y is either a hydrogen or a hydroxyl or ketone oxygen. All other atomic valences, or bonds, are assumed to be hydrogen atoms unless otherwise denoted above.

In one aspect, the invention provides a method for making a compound that is a C5 keto acid or ester, or a C5 hydroxy acid or ester, or cyclic derivative thereof. The method comprises converting pyruvate to a C5 intermediate by aldol addition, and converting the C5 intermediate to said compound through chemical or enzymatic steps or a combination thereof. In certain embodiments, the C5 compound has the general formula $C_5C_4(X)C_3C_2(Y)C_1(=O)(Z)$ or $C_5C_4(O_1)C_3C_2(Y)C_1(=O)(O_1)$ as described above. In certain embodiments, the compound is prepared from 5-carbon and/or 6-carbon sugars or feedstock suitable as carbon source for a microbial host. In these embodiments, the method comprises formation of pyruvate from the sugar or feedstock (e.g., by the microbial host), and aldol addition of acetylaldehyde to the pyruvate (e.g., in the microbial host or in a cell-free system), to thereby prepare a 5-carbon keto acid as an intermediate for the preparation of the desired C5 compound. Acetylaldehyde for aldol addition may be prepared by decarboxylation of pyruvate in the microbial host. The aldol addition product may be further subjected to one or more reduction, oxidation, dehydration, group transfer, hydrolysis and/or lactonization reactions (e.g., each independently in the microbial host or cell free system) to prepare the desired C5 product.

Such products may be used as building blocks to prepare commercially valuable chemicals and fuels. For example, lactones such as 2-oxo-valerolactone (compound L7 in FIG. 2), 2-hydroxy-valerolactone (compound L6 in FIG. 2), angelica lactones (compound L2, L3 and L10 in FIG. 2) and 4-valerolactone (γ-valerolactone, compound L1 in FIG. 2) can be used as solvents. Angelica lactone and 4-valerolactone can also be converted chemically to methylene methyl butyrolactone (MeMBL) (see for example WO/2006/015023, WO/2006/015024 for methods to catalyze this conversion). Methylene methyl butyrolactone can be used as a monomer or copolymer to increase the thermal tolerance of polymethylacrylate (PMMA) polymers used widely in electronics and automotive applications, or to manufacture polymers altogether (such as Poly(MeMBL), see for instance WO/2005/028529). In addition, 4-valerolactone can be converted using chemical catalysis to valeric acid and further valerate esters, as well as isomeric butenes, butadiene and other alkenes, including alkenes of eight carbons or more, as reviewed in Bozell J., *Connecting Biomass and petroleum Processing with a chemical bridge*, Science 329: 522-523 (2010). Levulinic Acid (compound P1 in FIG. 1) can be converted to 1,4 pentanediol and diphenolic acid, both of which can be used to manufacture polymers. δ-aminolevulinic acid (a derivative from Levulinic Acid) is a herbicide with an estimate market in excess of 300 pounds per year. Further still, Levulinic Acid can be converted to pyrrolidones (WO/2004/085048), pyrrolidinone (WO/2010/065833, WO/2004/085390, WO/2004/085349, WO/2004/084633), angelica lactone (WO/2005/097723), 4-valerolactone and 2-methyl-THF, which are end products or can be further transformed into other compounds with various utilities such as anionic liquids (WO/2010/065833), biofuels and fuel additives. Levulinic Acid can further be employed as a material for batteries (e.g. JP09190820), inks (U.S. Pat. No. 5,769,929), coatings (JP06280041), anti-corrosion coatings (EP496555) Levulinic esters (or levulinate esters, compounds P9 in FIG. 1) are polymer building blocks by themselves and after transformation to ketals (US 2008/0242721) and can also be used as fuel additives (as described in U.S. Pat. No. 7,153,996, which is hereby incorporated by reference in its entirety). In addition, levulinic esters can be used in personal care products (e.g. Japanese patent JP 05320023), surfactants and lubricants (EP882745), absorbents (see WO/1998/9843684). All references cited in this paragraph are hereby incorporated by reference.

Both levulinic acid, levulinic esters, and some of the lactones listed in FIG. 2 can also be used in the manufacture of pharmaceutically active ingredients, and pharmaceutical applications, some of which being listed in Bozell J., *Production of levulinic acid and use as a platform chemical for derived products*, Resources, Conservation and Recycling 28:227-239 (2000). For instance, WO/1995/022524 reports the use of levulinate methyl ester for the synthesis of novel indole derivatives used as anti-cancer agents. Levulinic acid and 4-hydroxy-pentanoic acid can also by used a chiral reagent, with a wide array of potential applications (see for example Meyers et al., *Stereoselective alkylations in rigid systems. Effect of remote substituents on p-facial additions to lactam enolates. Stereoelectronic and steric effects*, J. Am. Chem. Soc. 120:7429-7438 (1998). Pharmaceutical applications of the C5 produced by the invention may include the use of butyro- and valero-lactone derivatives as antibiotic and anti-biofilms agents through there interference with the quorum sensing molecular mechanism in bacteria (see for instance EP 1716131 and WO/2006/117113). Additional uses may derive from the biologically active proto-anemonin (compound L4 in FIG. 2). Finally, Levulinic Acid and esters have been used for food, flavor and fragrances (EP1533364) as well as additives in numerous consumer products. For example, Levulinic Acid is used as an additive in cigarettes (WO/2010/051076). All references in this paragraph are hereby incorporated by reference.

In certain embodiments of the invention, the method comprises converting pyruvate into 4-valerolactone. In another embodiment, the method comprises converting pyruvate into levulinic acid. In another embodiment, the method comprises converting pyruvate into levulinic esters (levulinates) such as, but not limited to, ethyl levulinate and propyl levulinate. In another alternative embodiment of the invention, the method comprises converting pyruvate into angelica lactone, alpha- and alpha'-angelica lactones. In still other embodiments, the method comprises converting pyruvate into 2,4-dihydroxy-pentanoic acid or its cyclized form, 2-hydroxy-4-valerolactone. In yet another embodiment, the method comprises converting pyruvate into 2-oxo-4-hydroxy-pentanoic acid or its cyclized form, 2-oxo-4-valerolactone.

In some embodiments of the invention, the method comprises multiple enzymatic steps integrated into a single metabolic pathway in a eukaryotic, prokaryotic or archaea fermentation host, including but not limited to *Saccharamyces* sp., *Pichia* sp., *Pseudomonas* sp., *Bacillus* sp., *Chrysosporium* sp., and *Escherichia coli*. In these and other embodiments, the method involves one or more enzymatic steps carried out in a cell-free system, or chemical catalysis steps, or a combination thereof, the various intermediates in the pathway being optionally separated and/or purified from the fermentation broth as necessary to complete the process.

An advantage of certain embodiments of the invention is that it builds on top of central metabolism. For instance, both C5 and C6 metabolism in eukaryotes, prokaryotes and archea can employ glycolysis to produce pyruvate. Pyruvate is one of the most important intermediates of central metabolism, and in addition to glycolysis can be obtained from lipid metabolism as well as amino-acid metabolism. The method of the invention takes pyruvate, and converts two molecules of pyruvate into one C5 molecule such as levulinic acid and 4-valerolactone. In the case of C6 sugars the carbon yield can be up to 80%. In the case of C5 sugars the carbon yield can be theoretically up to 100%. If the method employs a microbial strain capable of simultaneously fermenting C5 and C6 such as, but not limited to, engineered *Saccharomyces Cerevisae* and *Pichia Stipitis*, it allows the direct fermentation of sugars to levulinic acid, 4-valerolactone or any of the C5 compounds depicted in FIG. 1 and FIG. 2. This high achievable yield presents a decisive industrial advantage when compared to alternative thermochemical methods of obtaining levulinic acid or gamma-valerolactone which typically produce molar yields of 40% or less.

In one embodiment of the invention, the method converts a stream of sugars into one or several of the C5 compounds listed in FIGS. 1 and 2. In another embodiment, starch is used as feedstock for the process. In another embodiment, the method converts lignocellulosic feedstock (including, but not limited to, corn stover, wood chips, municipal waste, Pulp and Paper mill sludge) into at least one of the C5 compounds listed in FIGS. 1 and 2.

In one embodiment of the invention, the method converts C6 sugars into one or several of the C5 compounds listed in FIGS. 1 and 2, preferably in fermentation strains highly efficient at uptake and fermentation of C6 sugars, such as, but not limited to, *Saccharomyces cerevisiae*, Cargill's *CB*1 strain (as described in WO/2007/106524), *Pseudomonas*, *Chrysosporium* and *Escherichia coli* (*E. coli*). In another embodiment of the invention, the method converts C5 sugars to one or several of the C5 compounds listed in FIGS. 1 and 2, preferably in fermentation strains highly efficient at uptake and fermentation of C5 sugars, such as, but not limited to, engineered *Saccharomyces Cerevisiae* and *Pichia stipitis*. In an embodiment of the invention, the method simultaneously converts C5 and C6 sugars to the C5 compound, preferably in fermentation strains highly efficient at uptake and fermentation of both C5 and C6 sugars (e.g., *Saccharomyces cerevisiae*). In another embodiment of the invention, the fermentation strains show high level of tolerance to biomass hydrolysate inhibitors such as, but not limited to, furans and to low pH or high organic acid titer media.

In certain embodiments, the feedstock comprises one or more C6 sugars selected from allose, altrose, glucose, mannose, gulose, idose, talose, galactose, fructose, psicose, sorbose, and tagatose. In these or other embodiments, the feedstock comprises one or more C5 sugars selected from xylose, arabinose, ribose, lyxose, xylulose, and ribulose.

When the method of the invention is used to convert C5 and C6 sugars to 4-hydroxy-pentanoic acid or 4-valerolactone, the pathway is designed to be redox (reduction-oxidation) balanced: two reducing equivalents (formation of NAD(P)H) are produced during glycolysis to yield pyruvate (one glucose molecule to two pyruvate molecules) and two reducing equivalents are consumed (formation of NAD(P)) by the downstream process from pyruvate to 4-hydroxy-pentanoic acid or 4-valerolactone (γ-valerolactone). The fact that this pathway is redox balanced for the production of these two molecules will result in optimized conversion in the case of fermentation process, and reduce or remove the need to further engineer the fermentation host to counter inbalance. For the fermentation of sugars directly to all the other compounds or building blocks (FIG. 1), the fermentation host will rely on separate side reactions to balance the pathway or an external source of redox equivalent suitable to balance the pathway.

BRIEF DESCRIPTION OF THE DRAWINGS

FIG. 9 shows the HPLC traces obtained, with the peaks corresponding to the substrates and products indicated in the figure with the black arrow. The chemical identity of the product, 4-hydroxy, 2-oxo pentanoic acid was confirmed by LC/MS (data not shown).

DETAILED DESCRIPTION OF THE INVENTION

Figure 3:
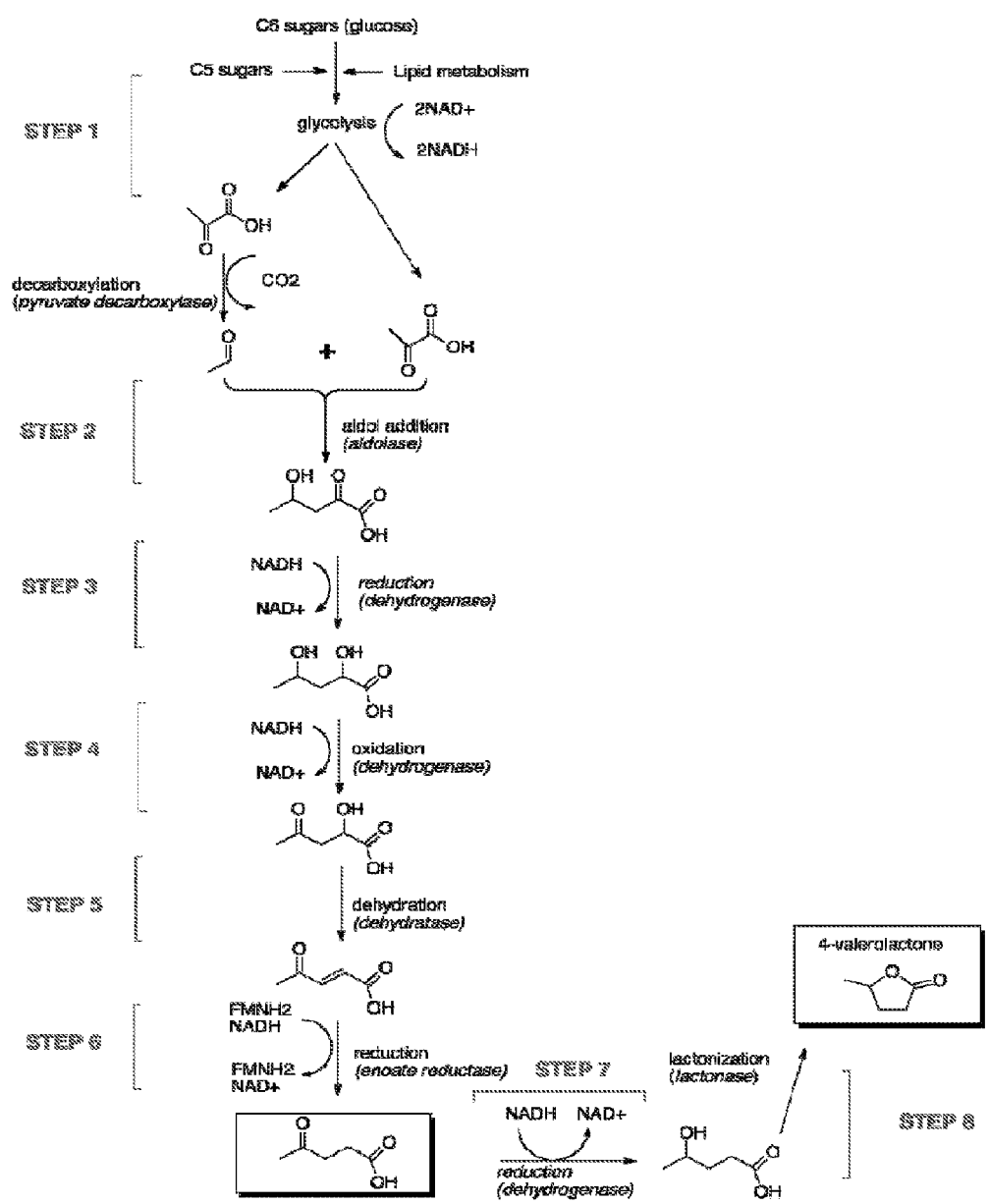
FIG. 3 provides a general view of the biochemical processes converting pyruvate to any of the C5 compounds of FIG. 1 or FIG. 2, with certain steps highlighted. Some possible chemical intermediates and subroutes are not depicted here. See FIG. 5 for a more exhaustive depiction of the different pathway possibilities.

In certain aspects and embodiments, the invention provides a chemical pathway for the conversion of pyruvate obtained from sugars or other carbon sources, to valuable C5 materials such as levulinic acid. Conceptually, the method of the invention provides a pathway that is organized in at least two steps, and in some embodiments, from 4 to 8 steps, such as 7 to 8 steps (see the core 8 steps depicted in FIG. 3), with up to 4 additional cyclization steps of intermediates obtained along the pathway. Attachment of the intermediate at multiple stages to a Co-enzyme A (CoA) moiety allows the pathway to lead to CoA intermediates such as levulinyl-CoA (see FIG. 6). In addition, four optional steps can lead to the cyclized variants of the key intermediates in the pathway (see again FIG. 6).

According to various embodiments, a first step is glycolysis, which converts sugars (such as from biomass) to pyruvate, or alternatively any chemical conversion from sugars to pyruvate. A second step converts two molecules of pyruvate into one molecule of 4-hydroxy 2-oxo-pentanoic acid and $CO_2$. An optional cyclization step produces the corresponding lactone, 2-oxo-4-valerolactone. An optional CoA attachment step can lead to 4-hydroxy-2-oxo pentanoyl-CoA. A third step reduces 4-hydroxy-2-oxo-pentanoic acid into 2,4-dihydroxy-pentanoic acid, or 4-hydroxy-2-oxo pentanoyl-CoA to 2,4-dihydroxy-pentanoyl-CoA, or 2-oxo-4-valerolactone to 2-hydroxy-4-valerolactone. An optional cyclization step produces the corresponding lactone, 2-hydroxy-4-valerolactone, from either 2,4-dihydroxy-pentanoic acid or 2,4-dihydroxy-pentanoyl-CoA. An optional CoA attachment step leads to 2,4-dihydroxy pentanoyl-CoA from 2,4-dihydroxy pentanoic acid. A fourth step oxidizes 2,4-dihydroxy-pentanoic acid to 2-hydroxy-4-oxo-pentanoic acid, or 2,4-dihydroxy-pentanoyl-CoA to 2-hydroxy-4-oxo-pentanoyl-CoA. An optional CoA attachment step converts 2-hydroxy-4-oxo-pentanoic acid to 2-hydroxy-4-oxo pentanoyl-CoA. A fifth step dehydrates 2-hydroxy-4-oxo-pentanoic acid to 4-oxo-2-pentenoic acid, or 2-hydroxy-4-oxo-pentanoyl-CoA to 4-oxo-2-pentenoyl-CoA. An optional CoA attachment step converts 4-oxo-2-pentenoic acid to 4-oxo-2-pentenoyl-CoA. An optional step reduces further 4-oxo-2-pentenoic acid to 4-hydroxy-2-pentenoic acid, or 4-oxo-2-pentenoic acid to 4-hydroxy-2-pentenoyl-CoA, both of which can be optionally cyclized to produce angelica lactone. Another optional CoA attachment step leads to 4-hydroxy-2-pentenoyl-CoA from 4-hydroxy-2-pentenoic acid, which again can be optionally cyclized to produce angelica lactone. An alternative embodiment of the invention "collapses" the fourth and fifth step into one single step. A sixth step yields levulinic acid (4-hydroxy-pentanoic acid) through the reduction of 4-oxo-2-pentenoic acid in a similar manner as above. An optional step attaches coenzyme A (CoA) to levulinic acid leading to levulinyl-CoA. Levulinyl-CoA can then be transformed into a variety of levulinic esters through the use of a transferase reacting with the appropriate alcohol. In some embodiments, a seventh step further reduces levulinic acid to produce 4-hydroxy-pentanoic acid. An eighth step cyclizes 4-hydroxy-pentanoic acid to yield 4-valerolactone.

Figure 4:
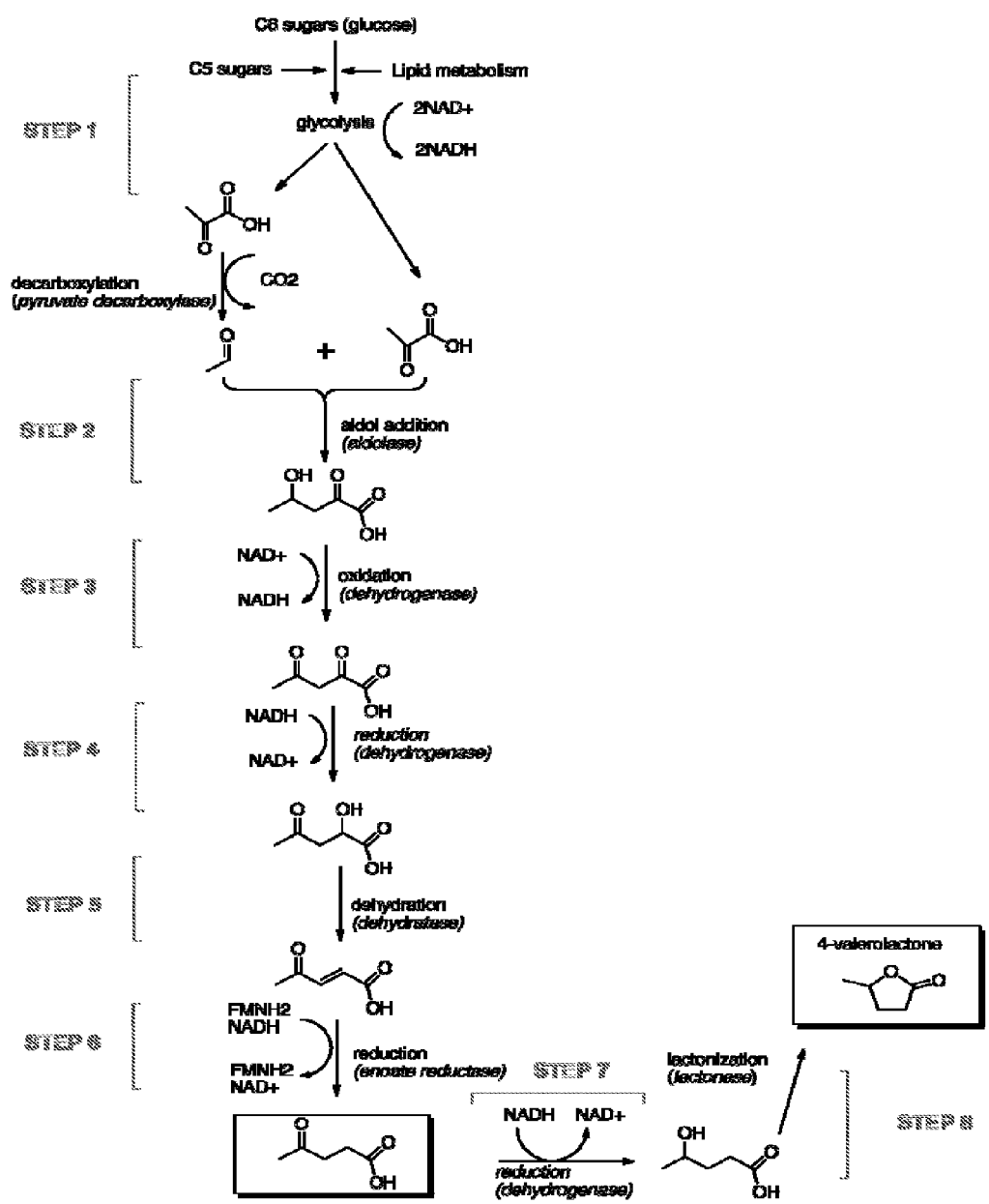
FIG. 4 provides a general view of the biochemical pathway and processes according to certain embodiments of the invention, where the order of the oxidation/reduction steps (corresponding to steps 3 and 4 in FIG. 3) is inverted. As in FIG. 3, some possible chemical intermediates and sub-routes are not depicted here. See FIG. 6 for a more exhaustive depiction of the different pathway possibilities different pathway possibilities.

In certain embodiments, steps 4 and 5 can be carried out in a single transformation, an oxidative dehydration. In another embodiment of the invention, steps 3 and 4 are reversed in order so that 2-hydroxy-4-oxo-pentanoic acid is first oxidized into 2,4-dioxo-pentanoic acid, and further reduced to 2-oxo-4-hydroxy-pentanoic acid, so that the pathway of FIG. 3 becomes the one represented in FIG. 4.

Figure 6:
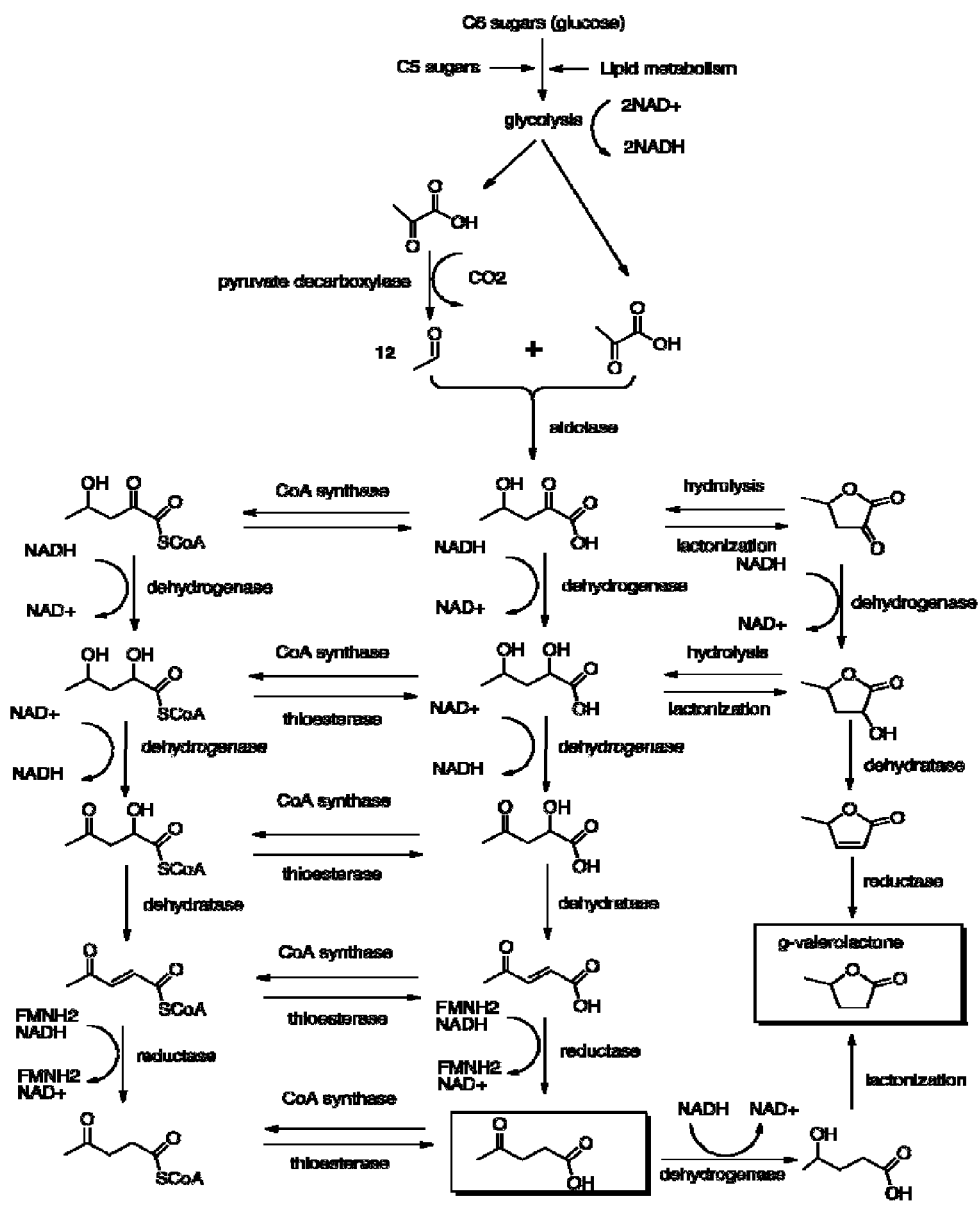
FIG. 6 provides a detailed view of the biochemical pathway/processes converting pyruvate to any of the C5 compounds or building blocks of FIG. 1 or 2. In addition to the chemical steps depicted in FIGS. 3, 4, and 5, different cyclic intermediates that can be obtained from cyclization reaction from the intermediates from the core pathway are depicted, as well as chemical transformation that lead from the cyclic lactone intermediates to the various C5 compounds or building blocks. Additionally, different CoA intermediates that can be obtained from the intermediates in the core pathway are also represented. The pathway can be used to produce levulinyl-CoA, from which either levulinic acid and 4-valerolactone, or levulinate and/or other pentanoate esters such as 4-oxo-pentanoate ester (compound P9) in FIG. 1, can readily be obtained.
Figure 7:
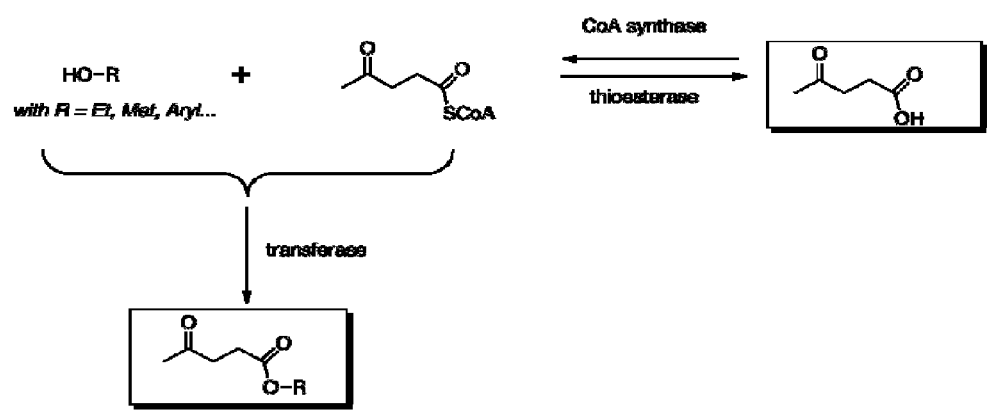
FIG. 7 shows the principle of production of levulinic esters (levulinates) and levulinic acid from the levulinyl-CoA intermediate through the action of either a thioesterase or a transferase. The side chain R can be any functional group such as, but not limited to methyl, ethyl, propyl, aryl, phenyl, naphthyl and other aromatic groups, as well as alkyl group with oxygen and nitrogen substituents such as ketones, primary, secondary and tertiary alcohols, primary, secondary and tertiary amines, etc.
Figure 8:
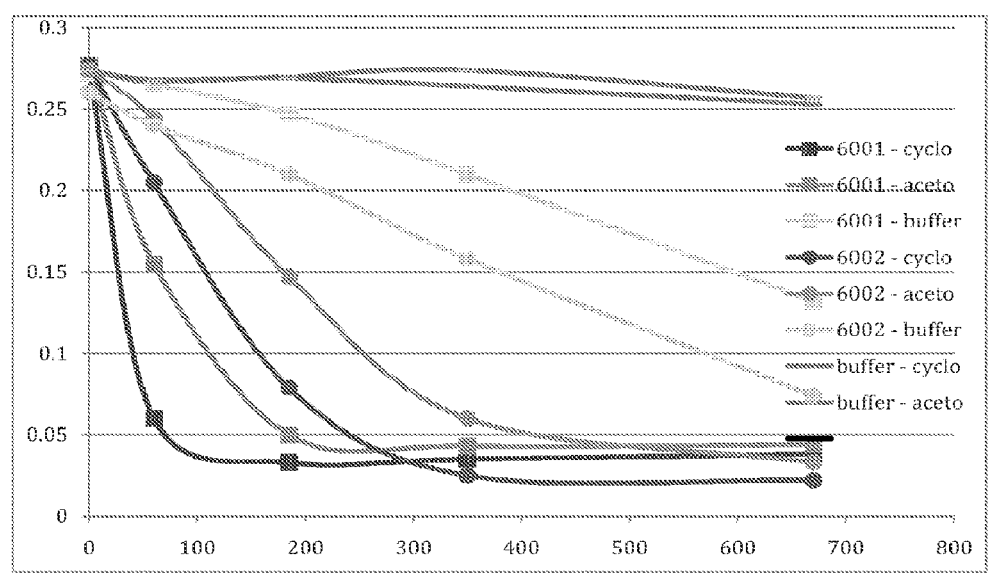
FIG. 8 shows the kinetic traces obtained when reacting two enoate reductase enzymes (Genbank accession numbers AAA64522 and AAD16106, labeled 6001 and 6002 in FIG. 8) with substrate 4-oxo-2-pentenoic acid (also known as acetylacrylic acid, see compound P2 in FIG. 1) and substrate cyclohexenone as a control. The curve labeled "6001 aceto" and "6002 aceto" show activity of the proteins in presence of 100 uM NADPH and the substrate 4-oxo-2-pentenoic acid. The curve labelled "6001 cyclo" and "6002 cyclo" show the activity of the proteins in presence of 100 uM NADPH and the substrate cyclohexenone. The decrease of absorption at 340 nm, measuring the conversion of NADPH to the oxidized form NADP+, is monitored. This curve shows the conversion of the substrate 4-oxo-2-pentenoic acid to levulinic acid (compound P1 in FIG. 1) by both proteins. Control curves (labelled "6001 buffer" and "6002 buffer" and "buffer cyclo" and "buffer aceto") show the decrease in absorbance with the substrates alone in buffer or the proteins alone in buffer. No significant activity is detected under these conditions. All curves obtained in buffer Potassium Phosphate 100 mM, pH 7.0 and room temperature (25° C.). Initial NADPH concentration 100 uM, 4-oxo-2-pentenoic acid initial concentration 100 mM, cyclohexenone initial concentration 50 mM. Protein concentration varied.
Figure 9:
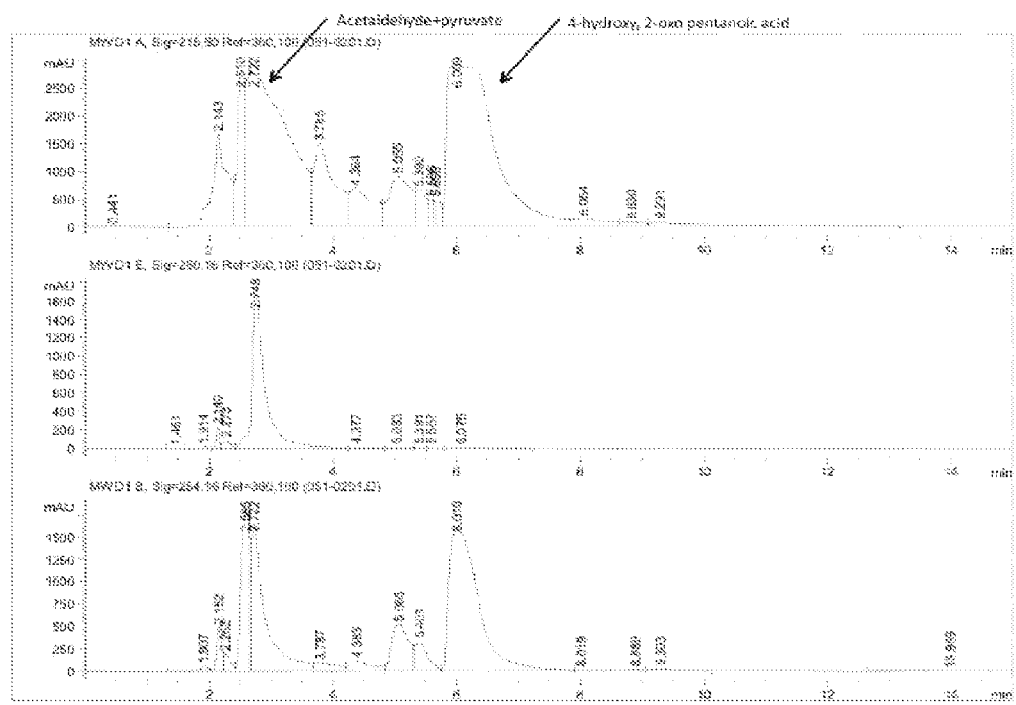
FIG. 9 demonstrates the activity of a class II aldolase enzyme from *Pseudomonas Putida*, HpaI aldolase (Genbank accession number ADA63518) on substrates acetaldehyde and pyruvate. Assay conditions were as follows: the protein was expressed and Ni-purified from *E. Coli* and reacted with a mix of acetaldehyde and pyruvate at an initial concentration of 100 mg/ml, in Tris buffer, pH 8.0 supplemented with 100 mM $MnCl_2$. The protein and the substrates were incubated at room temperature for 30 min before quenching with HCl and run on an HPLC with an EPIC polar column.

In another embodiment of the invention, steps 3, 5 and 6 (FIG. 3) are carried out directly on the respective lactones L1, L2, L6, L7, L8, L9 and L10, where the branching from linear intermediates produced initially from pyruvate and acetaldehyde occurs at any one of the cyclization steps described in FIG. 6. This embodiment of the invention can be used either to obtain lactones directly, or, after hydrolysis, to obtain back any of the compounds P1 to P16 (including levulinic acid).

In yet another aspect of the invention, steps 2, 3, 4, 5 and 6 (FIG. 3) are carried out on the CoA intermediates, where the branching from linear intermediates produced initially from pyruvate and acetaldehyde occur at any one of the CoA attachment steps described in paragraph FIG. 6. This embodiment of the invention can be used to obtain any of the compounds P1 to P16 (including levulinic acid) through the use of thioesterases. Levulinic esters (P9) can be obtained from levulinyl-CoA and the appropriate alcohol by the use of a transferase.

Step 1: Conversion of Sugars to Pyruvate

The conversion of sugars to pyruvate is part of the well-studied metabolic pathway, glycolysis. In glycolysis, the action of multiple enzymes results in the conversion of each molecule of C6 sugar such as glucose to two molecules of pyruvate, two molecules of ATP and two reducing equivalent in the form of two NAD(P)H molecules.

In one embodiment of the invention, pyruvate is obtained from glycolysis in a fermentation organism and subsequently used in the downstream pathway in the fermentation host. In an alternative embodiment, pyruvate is separated from the fermentation broth and subsequently processed according to the downstream pathway.

Step 2: Conversion of Pyruvate to 4-Hydroxy-2-Oxo-Pentanoic Acid 4-hydroxy-2-oxo-pentanoic acid can be produced by the aldol addition of acetaldehyde (an aldehyde) to pyruvate (an α keto-acid). The addition reacts one equivalent of acetaldehyde with one equivalent of pyruvate. Acetyladehyde can be obtained in various ways. For example, pyruvate decarboxylase catalyzes the non-oxidative decarboxylation of pyruvate to acetaldehyde. Pyruvate decarboxylase from multiple eukaryotic or prokaryotic sources (e.g. *Saccharomcyes cerevisiae*) can therefore be used. In a preferred embodiment of the invention, acetyladehyde is produced from pyruvate with the enzyme pyruvate decarboxylase.

Multiple aldolase have been isolated that have been shown to catalyze the aldol addition between pyruvate and acetaldehyde. A class I aldolase, 4-hydroxy-2-keto-pentanoic acid aldolase (HKP aldolase) is an aldolase employing a Schiff base lysine and catalyzes the forward and reverse reaction. In one embodiment of the invention, the aldol addition between pyruvate and acetaldehyde is catalyzed by HKP aldolase from *E. coli* described in Pollard, J R et al., *Substrate selectivity and biochemical properties of 4-hydroxy-2-keto-pentanoic acid aldolase from E. Coli*, Appi. And Environ. Microbiology, 64(10):4093-4094 (1998), or a homolog thereof, or mutants thereof (those mutants optionally being obtained by protein engineering using computational design, directed evolution techniques or rational mutagenesis, or a combination thereof). Computational design techniques are disclosed in US 2009-0191607 and WO 2010/077470, which are hereby incorporated by reference in its entirety.

There are at least two class II aldolases known to catalyze the addition between pyruvate and acetaldehyde, and two (BphI and HpaI) have been characterized in some level of detail in Wang W et al., *Comparison of two metal-dependent pyruvate aldolases related by convergent evolution: substrate specificity, kinetic mechanism and substrate channeling*, Biochemistry, 49:3774-3782 (2010). These enzymes employ a metal co-factor (either Zn or Mn are common). BphI and HpaI share no detectable sequence similarity. Whereas BphI is stereoselective and leads to the 4S adduct, HpaI, due to its very open active site, produces a racemic mixture (4R and 4S adducts). BphI is allosterically coupled to BphJ, an acetaldehyde dehydrogenase, and is not active and stable when expressed in isolation. HpaI however, is expressable in *E. coli* by itself and shows activity. In an alternate embodiment of the invention, the aldol addition between pyruvate and acetaldehyde is catalyzed by HpaI or BphI, or mutants thereof (those mutants optionally being obtained by protein engineering using computational design, directed evolution techniques or rational mutagenesis, or a combination of the three).

As an extension, any suitable pyruvate aldolase and other similar aldolases (e.g. KDPG aldolase) catalyzing the aldol addition of an aldehyde to a ketone can conceivably be reengineered to catalyze the aldol addition of acetaldehyde to pyruvate. The redesign may include, but is not limited to, achieving the desired substrate specificity for both pyruvate and acetaldehyde, controlling the desired stereoselectivity to produce either a racemic or enantiopure adducts ((R)4-hydroxy-2-oxo-pentanoic acid and (S)4-hydroxy-3-oxo-pentanoic acid), stabilizing the enzyme to obtain the desired catalytic activity in the industrial conditions in which the invention is practiced (e.g. thermostabilization or stabilization in higher organic titer), and/or improving the enzyme expressability and solubility in the context of the industrial conditions in which the invention is practiced (e.g. in a metabolic pathway in *Saccharomyces cerevisiae*). In another embodiment of the invention, the aldol addition between pyruvate and acetaldehyde is catalyzed by pyruvate aldolase, or any homologs and mutants thereof (those mutants optionally being obtained by protein engineering using computational design, directed evolution techniques or rational mutagenesis, or a combination of the three).

Finally, using the technique of de novo enzyme design such as the one described in Zanghellini, A et al, *New Algorithms and an in silico Benchmark for Computational Enzyme Design*, Protein Science 15:2785-2794 (2006), it is possible to design new aldolase enzymes for substrates that may or may not exist in nature. Up to 70 such aldolases have been designed de novo as described in US 2009-0191607, which is hereby incorporated by reference in its entirety. The application of this methodology to the substrates pyruvate and acetaldehyde can lead to aldolases with the desired activity. In another embodiment of the invention, the aldol addition between pyruvate and acetaldehyde is catalyzed by a de novo designed aldolase.

Figure 1:
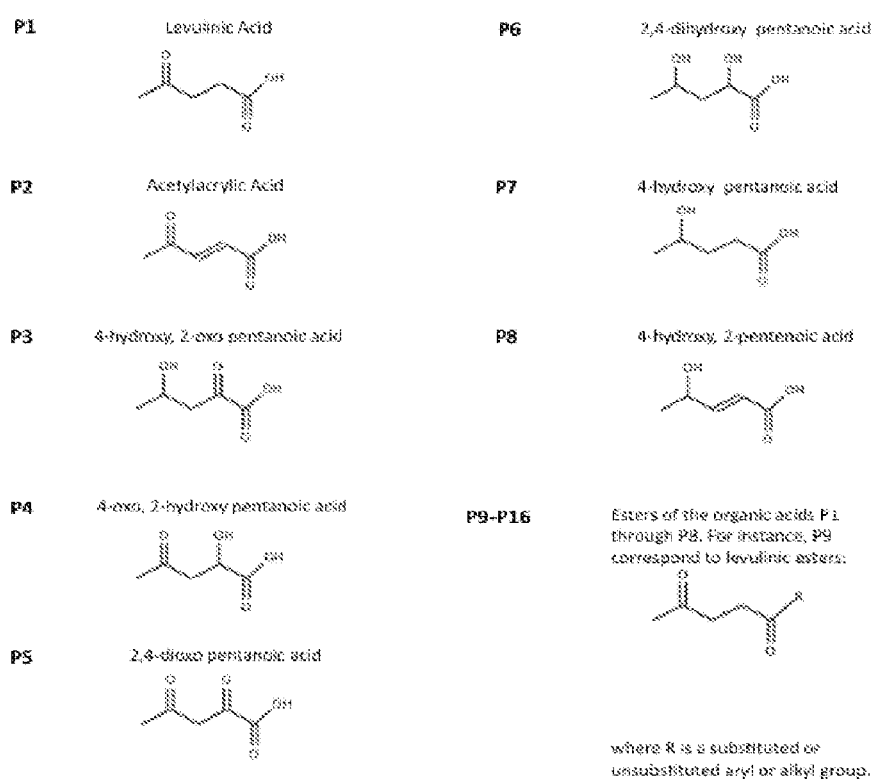
FIG. 1 shows the molecular formulae for levulinic acid (compound P1 in FIG. 1), as well as valuable derivatives that can be produced at different steps in the pathway and in various embodiments of the processes described herein (compounds P1 to P16 in FIG. 1).
Figure 2:
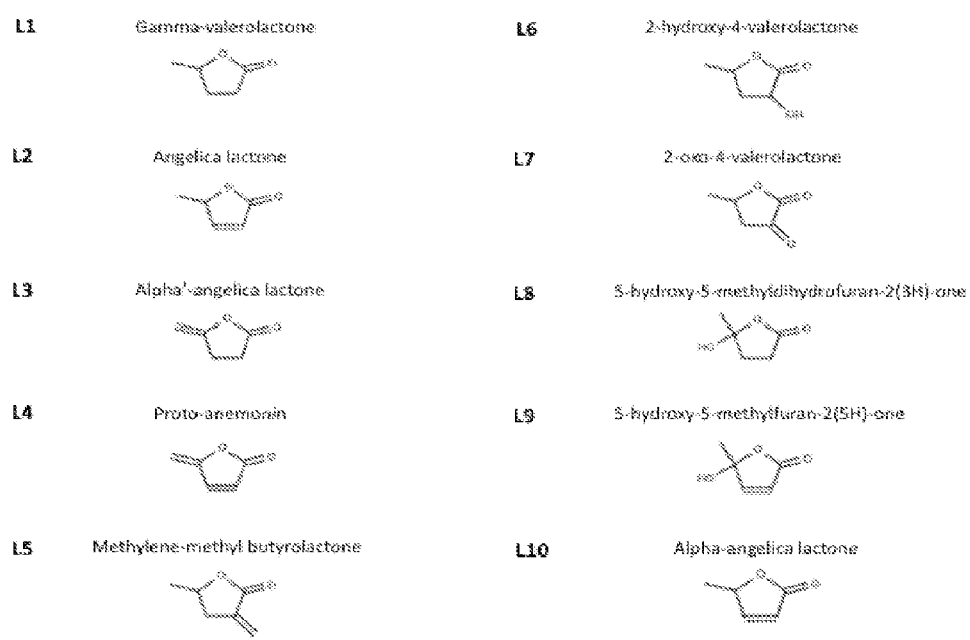
FIG. 2 shows the molecular formulae for various C5 lactones that can be produced at different steps in the pathway according to various embodiments of the method (compounds L1 to L10).

Step 2': cyclization of 4-hydroxy-2-oxo-pentanoic acid to 2-oxo-4-valerolactone 4-hydroxy-2-oxo-pentanoic acid is cyclized into 2-hydroxy-4-valerolactone (compound L7 in FIG. 1). In acidic to neutral solutions, the thermodynamical equilibrium lies towards the cyclization to the lactone. The cyclization to the lactone can be kinetically enhanced by the use of either chemical or biochemical catalysis. Homogeneous and heterogeneous catalysts for lactonization include strong acid conditions (e.g. sulfuric acid), metal catalysts (e.g. palladium, rhubidium). Biochemical catalysis can be obtained by the action of lipases, esterases, proteases and lactonases under conditions that favor the forward lactonization reaction (low to neutral pH/high organic solvent titer) as demonstrated for example in Martin C H, et al, *Integrated bioprocessing for pH-dependent of 4-valerolactone from levulinate in Pseudomonas Putida KT2440, appl. and Environ, Microbiology* 76(2):417-424.

In one embodiment of the invention, 2-oxo-4-valerolactone is produced from 4-hydroxy-2-oxo-pentanoic acid, in the presence of a catalyst, after separation of 4-hydroxy-2-oxo-pentanoic acid from the fermentation broth or cell-free solution. In another embodiment of the invention, the lactonization of 4-hydroxy-2-oxo-pentanoic acid to 2-oxo-4-valerolactone is catalyzed directly by a lipase or esterase or protease or lactonase, or mutants thereof (those mutants being optionally obtained by protein engineering using computational design, directed evolution techniques, rational mutagenesis, or a combination of the three).

Step 3: reduction of 4-hydroxy-2-oxo-pentanoic acid to 2,4-dihydroxy-pentanoic acid Among the wide variety of natural dehydrogenases, in silico and/or experimental screening can select dehydrogenases with substrate specificity that tolerates 4-hydroxy-2-oxo-pentanoic acid and 2,4-dihydroxy-pentanoic acid. In addition, computational design, directed evolution techniques or rational mutagenesis, or a combination of the three, can be used to alter or increase the substrate specificity of existing dehydrogenase towards 4-hydroxy-2-oxo-pentanoic acid and 2,4-dihydroxy-pentanoic acid. Examples of suitable dehydrogenase starting points include L- and D-lactate dehydrogenases (NAD(P)H— or Heme-dependent, from eukaryotic or bacterial origin), malate, aspartate and glutamate dehydrogenases (NAD(P)H-dependent from eukaryotic or bacterial origin), as well as alcohol dehydrogenases (such as NAD(P)H-dependent alkyl or phenyl alcohol dehydrogenases). Examples of such dehydrogenases are listed in the example section.

In one embodiment of the invention, 4-hydroxy-2-oxo-pentanoic acid is selectively reduced to 2,4-dihydroxy-pentanoic acid using homogenous or heterogeneous chemical catalysis. 2,4-dihydroxy-pentanoic acid may or may not be separated/purified from the fermentation or cell-free solution to complete this step. Preferably, 2,4-dihydroxy-pentanoic acid is separated from the solution or fermentation broth before being subsequently subjected to said reduction.

In one embodiment of the invention, a NAD(P)H-dependent dehydrogenase is used to catalyze the reduction of the ketone at the 2 position in 4-hydroxy-2-oxo-pentanoic acid. In another embodiment, said dehydrogenase reduces the ketone with a high degree of substrate specificity for 4-hydroxy-2-oxo pentanoic acid and high regioselectively for the ketone at the 2 position. In one embodiment of the invention, said dehydrogenase is not stereoselective and can accept both 4R and 4S enantiomers. In another embodiment of the invention, said dehydrogenase reduces selectively either the 4R or 4S enantiomeric form of 4-hydroxy-2-oxo-pentanoic acid.

In another embodiment of the invention, a FAD-dependent dehydrogenase is used instead of a NAD(P)H-dependent dehydrogenase, preferably with a high degree of substrate and regioselectivity. In one embodiment of the invention, said dehydrogenase is not stereoselective and can accept both 4R and 4S enantiomers. In another embodiment of the invention, said dehydrogenase reduces selectively either the 4R or 4S enantiomeric form of 4-hydroxy-2-oxo-pentanoic acid.

In another embodiment of the invention, a FMN-dependent dehydrogenase is used instead of a NAD(P)H-dependent dehydrogenase, preferably with a high degree of substrate and regioselectivity. In one embodiment of the invention, said dehydrogenase is not stereoselective and can accept both 4R and 4S enantiomers. In another embodiment of the invention, said dehydrogenase reduces selectively either the 4R or 4S enantiomeric form of 4-hydroxy-2-oxo-pentanoic acid.

In yet another embodiment of the invention, a ferricytochrome-dependent dehydrogenase is used instead of a NAD(P)H-dependent dehydrogenase, preferably with a high degree of substrate and regioselectivity. In one embodiment of the invention, said dehydrogenase is not stereoselective and can accept both 4R and 4S enantiomers. In another embodiment of the invention, said dehydrogenase reduces selectively either the 4R or 4S enantiomeric form of 4-hydroxy-2-oxo-pentanoic acid.

In yet another embodiment of the invention, a quinone-dependant dehydrogenase is used instead of a NAD(P)H-dependent dehydrogenase, preferably with a high degree of substrate and regioselectivity. In one embodiment of the invention, said dehydrogenase is not stereoselective and can accept both 4R and 4S enantiomers. In another embodiment of the invention, said dehydrogenase reduces selectively either the 4R or 4S enantiomeric form of 4-hydroxy-2-oxo-pentanoic acid.

Step 3': cyclization of 2,4-dihydroxy-pentanoic acid to 2-hydroxy 4-valerolactone 2,4-dihydroxy-pentanoic acid is cyclized into 2-hydroxy-4-valerolactone (compound L6 in FIG. 1). In acidic to neutral solutions, the thermodynamical equilibrium lies towards the cyclization to 4-valerolactone. The same remarks about thermodynamic equilibrium and chemical and biochemical catalysis hold as described above.

In one embodiment of the invention, 2-hydroxy-4-valerolactone is produced from 2,4-dihydroxy-pentanoic acid, in the presence of a catalyst, after separation of 2,4-dihydroxy-pentanoic acid from the fermentation broth or cell-free solution. In another embodiment of the invention, the lactonization of 2,4-dihydroxy-pentanoic acid to 2-hydroxy-4-valerolactone is catalyzed directly by a lipase or esterase or protease or lactonase, or mutants thereof (those mutants being obtained by protein engineering using computational design, directed evolution techniques or rational mutagenesis, or a combination of the three).

Step 4: oxidation of 2,4-dihydroxy-pentanoic acid to 4-oxo-2-hydroxy-pentanoic acid In one embodiment of the invention, 2,4-dihydroxy-pentanoic acid is selectively oxidized to 4-oxo-2-hydroxy-pentanoic acid using homogenous or heterogeneous chemical catalysis. 2,4-dihydroxy-pentanoic acid may or may not be separated/purified from the fermentation or cell-free solution to complete this step. Preferably, 4-oxo-2-hydroxy-pentanoic acid is separated from the solution or fermentation broth before being subsequently subjected to said oxidation.

In a preferred embodiment of the invention, an NAD(P)H-dependent dehydrogenase is used to catalyze the oxidation of the hydroxyl at the 4 position in 2,4-dihydroxy-pentanoic acid. In a preferred embodiment, said dehydrogenase oxidizes the hydroxyl with a high degree of substrate specificity for 2,4-dihydroxy pentanoic acid and high regioselectively for the hydroxyl at the 4 position. Preferably, said dehydrogenase accepts the four different enantiomers (2R4R,2R4S, 2S4R,2S4S) of 2,4-dihydroxy pentanoic acid. In an alternative embodiment, said dehydrogenase is oxidizing selectively either the 2R (2R4R,2R4S) or 2S (2S4R,2S4S) enantiomers of 2,4-dihydroxy-pentanoic acid, whichever is the most abundant enantiomer resulting from the previous reduction of 4-hydroxy-2-oxo-pentanoic acid. Examples of such dehydrogenases are listed in the example section.

In another embodiment of the invention, a FAD-dependent dehydrogenase is used to catalyze the oxidation of the hydroxyl at the 4 position in 2,4-dihydroxy-pentanoic acid. In a preferred embodiment, said dehydrogenase oxidizes the hydroxyl with a high degree of substrate specificity for 2,4-dihydroxy-pentanoic acid and high regioselectively for the hydroxyl at the 4 position. Preferably, said dehydrogenase accepts the four different enantiomers (2R4R,2R4S, 2S4R,2S4S) of 2,4-dihydroxy-pentanoic acid. In a alternative embodiment, said dehydrogenase is oxidizing selectively either the 2R (2R4R,2R4S) or 2S (2S4R,2S4S) enantiomers of 2,4-dihydroxy-pentanoic acid, whichever is the most abundant enantiomer resulting from the reduction of 4-hydroxy-2-oxo-pentanoic acid.

In another embodiment of the invention, a FMN-dependent dehydrogenase is used to catalyze the oxidation of the hydroxyl at the 4 position in 2,4-dihydroxy-pentanoic acid. In a preferred embodiment, said dehydrogenase oxidizes the hydroxyl with a high degree of substrate specificity for 2,4-dihydroxy-pentanoic acid and high regioselectively for the hydroxyl at the 4 position. Preferably, said dehydrogenase accepts the four different enantiomers (2R4R,2R4S, 2S4R,2S4S) of 2,4-dihydroxy-pentanoic acid. In a alternative embodiment, said dehydrogenase is oxidizing selectively either the 2R (2R4R,2R4S) or 2S (2S4R,2S4S) enantiomers of 2,4-dihydroxy-pentanoic acid, whichever is the most abundant enantiomer resulting from the reduction of 4-hydroxy-2-oxo-pentanoic acid.

In yet another embodiment of the invention, a ferricytochrome-dependent dehydrogenase is used to catalyze the oxidation of the hydroxyl at the 4 position in 2,4-dihydroxy-pentanoic acid. In a preferred embodiment, said dehydrogenase oxidizes the hydroxyl with a high degree of substrate specificity for 2,4-dihydroxy-pentanoic acid and high regioselectively for the hydroxyl at the 4 position. Preferably, said dehydrogenase accepts the four different enantiomers (2R4R,2R4S, 2S4R,2S4S) of 2,4-dihydroxy-pentanoic acid. In an alternative embodiment, said dehydrogenase is oxidizing selectively either the 2R (2R4R,2R4S) or 2S (2S4R, 2S4S) enantiomers of 2,4-dihydroxy-pentanoic acid, whichever is the most abundant enantiomer resulting from the reduction of 4-hydroxy-2-oxo-pentanoic acid.

In yet another embodiment of the invention, a quinone-dependent dehydrogenase is used to catalyze the oxidation of the hydroxyl at the 4 position in 2,4-dihydroxy-pentanoic acid. In a preferred embodiment, said dehydrogenase oxidizes the hydroxyl with a high degree of substrate specificity for 2,4-dihydroxy pentanoic acid and high regioselectively for the hydroxyl at the 4 position. Preferably, said dehydrogenase accepts the four different enantiomers (2R4R,2R4S, 2S4R,2S4S) of 2,4-dihydroxy-pentanoic acid. In a alternative embodiment, said dehydrogenase is oxidizing selectively either the 2R (2R4R,2R4S) or 2S (2S4R,2S4S) enantiomers of 2,4-dihydroxy-pentanoic acid, whichever is the most abundant enantiomer resulting from the reduction of 4-hydroxy-2-oxo-pentanoic acid.

Step 5: dehydration of 4-oxo-2-hydroxy-pentanoic acid to 4-oxo-2-pentenoic acid

Classically, chemical dehydration is achieved with either homogeneous or heterogeneous catalysis, such as temperature>100° C., concentrated acid (4.0M sulfuric acid) and/or metal oxide catalyst (zinc or aluminium oxides). In one embodiment of the invention, 4-oxo-2-hydroxy-pentanoic acid obtained after the reduction and oxidation steps is dehydrated chemically to 4-oxo-2-pentenoic acid by homogeneous or heterogeneous catalysis. 4-oxo-2-hydroxy-pentanoic acid may or may not be separated/purified from the fermentation or cell-free solution to complete this step. Preferably, 4-oxo-2-hydroxy-pentanoic acid is separated from the solution or fermentation broth before being subjected to said dehydration.

The dehydration of organic compounds can alternatively be catalyzed by a dehydratase enzyme. Several classes of dehydratase have been characterized and rely on different mechanisms: radical based mechanism such as in vitamin B12-dependent or SAM-dependent dehydratases (e.g. diol dehydratase, glycerol dehydratase), Lewis-acid mechanism such Iron-Sulfur containing dehydratases (e.g. dihydroxy-acid dehydratase, aconitase) and enolate ion intermediate mechanism such as diacid dehydratase (e.g. tartrate dehydratase). Whereas all mechanisms are applicable to the dehydration of 4-oxo-2-hydroxy-pentanoic acid, mechanisms relying on an enolate intermediate are preferred because the formation of an enolate anion on the carbonyl R to the hydroxyl being eliminated lowers the pKa of the α-proton, thereby allowing it to be readily abstracted by a general acid/base group. An additional general acid/base group protonates the leaving water molecule. This mechanism is exploited by a wide variety of natural dehydratases: Magnesium-dependent dehydratases from the enolase superfamily, such as tartrate dehydratase, gluconate dehydratase, use this mechanism for the dehydration of structurally diverse diacids with high substrate specificity, as described for instance in Gerlt et al., *Divergent evolution in the enolase superfamily: the interplay of mechanism and specificity*, Biochemistry, 433:59-70 (2005). Fumarase (also known as fumarate hydratase) catalyzes the enolate-based reversible hydration of malate to fumarate. Enoyl dehydratase (also known as crotonase) uses the enolate anion of a CoA thioester to catalyze the reversible hydration of various CoA substrates (see for instance Holden et al., *The Crotonase Superfamily: divergently related enzymes that catalyze different reactions involving acyl Coenzyme A thioesters*, Acc. Chem. Res. 34:145-157. (2001))

In one embodiment of the invention, the dehydration of 4-oxo-2-hydroxy-pentanoic acid to 4-oxo-2-pentenoic acid is catalyzed by a dehydratase. In a preferred embodiment of the invention, said dehydratase uses an enolate intermediate to catalyze the dehydration. Preferably, said dehydratase is a member of the enolase superfamily, fumarase or enoyl-coA dehydratase superfamilies, or mutants thereof obtained by protein engineering. In a preferred embodiment of the invention, said dehydratase exhibits a high level of substrate specificity for 4-oxo-2-hydroxy-pentanoic acid. In another preferred embodiment of the invention, said dehydratase dehydrates equally the 2R and 2S enantiomers of 4-oxo-2-hydroxy-pentanoic acid. In an alternative embodiment of the invention, said dehydratase dehydrates selectively either the 2R or 2S enantiomer of 4-oxo-2-hydroxy-pentanoic acid.

Alternative to Step 4 and 5:

Alternatively to a 2-step conversion of 2,4-dihydroxy-pentanoic acid to 4-oxo-2-pentenoic acid, a 1-step conversion can be achieved using an oxidative dehydration. Oxidative dehydrations are common in the metabolism of sugars. The so-called 4,6 dehydratase enzymes, such as UDP-GlcNAc-inverting 4,6-dehydratase which structural details are described in Ishiyama et al., *Structural studies of FlaA1 from helicobacter pylori reveal the mechanism for inverting 4,6-dehydratase activity*, J. Bio. Chem. 281(34):24489-24495 (2006). In one embodiment of the invention, such a 4,6-dehydratase is used to catalyze the oxidative dehydration of 2,4-dihydroxy-pentanoic acid to 4-oxo-2-pentenoic acid. In one aspect of the invention, said 4,6-dehydratase is enantioselective and dehydrates preferably one of the enantiomers of 2,4-dihydroxy-pentanoic acid (either 2R4R,2R4S, 2S4R or 2S4S). In another aspect of the invention, said 4,6-dehydratase is not enantioselective and dehydrates with similar catalytic efficiency two or more of the enantiomers of 2,4-dihydroxy-pentanoic acid. In a preferred embodiment of the invention, the 4,6-dehydratase is highly active on 2,4-dihydroxy-pentanoic acid is obtained from a natural 4,6-dehydratase by protein engineering using computational design, directed evolution techniques or rational mutagenesis, or a combination thereof.

Step 6: reduction of 4-oxo-2-pentenoic acid to 4-oxo-pentanoic acid (levulinic acid)

Double bonds on substituted alkenes can be reduced (hydrogenated) to obtain the corresponding saturated alkanes. Substituted alkenes can be reduced using chemical catalysis or, generally asymmetrically, using biocatalysts such as enoate reductases as reviewed in Stuermer et al., *Asymmetric bioreduction of activated C=C bonds using enoate reductases from the old yellow enzyme family*, Curr. Opin. In Chem. Bio. 11:203-213 (2007). Enoate reductases have been characterized from both eukaryotic, such as *Sacharomyces cerevisiae* and *Marchantia* and prokaryotic organisms, such as *Clostridium*. The family of enoate reductase enzymes is dependent on a flavin cofactor (FMN) that gets oxidized at each turnover of the enzyme. Except for one known case, which is nicotinamide-independent, the flavin cofactor is in turned reduced by a nicotinamide cofactor, either NADH or NADPH, that also binds in the active site. Upon completion of one turnover, the substrate has been reduced whereas the cofactor NAD(P)H has been oxidized to NAD(P)+. Enoate reductases differ in their substrate specificity. However, several enoate reductases such as yeast and *Clostridium* enoate reductases have a broad substrate specificity and can accommodate linear substituted alkenes (with acids or ketone functional groups) as well as substituted lactones such as 4-valerolactone.

In one embodiment of the invention, 4-hydroxy-2-oxo-pentanoic acid is separated from the separation broth or cell-free solution and the double bond selectively reduced using homogenous or heterogeneous catalysis.

In another embodiment of the invention, an enoate reductase enzyme is used to reduce 4-hydroxy-2-oxo-pentanoic acid into levulinic acid. In a preferred embodiment, said enoate reductase is dependent on both FMNH2 and NAD(P)H cofactors, said NAD(P)H cofactor being used in the active site to regenerate FMNH2 to its oxidoreduction state before catalysis. In a preferred embodiment of the invention, said enoate reductase is cloned and expressed in the fermentation host. In a alternative embodiment, said enoate reductase is used extracellularly, or in a cell-free system with an adequate cofactor regeneration system. In another alternative embodiment, said reduction is catalyzed by a whole cell catalyst expressing one or several enoate reductases, such that said cell is different from the fermentation host cell(s) in which part or the totality of the pathway is used.

Step 7: reduction of 4-oxo-pentanoic acid (levulinic acid) to 4-hydroxy-pentanoic acid Similarly to step 3, the reduction of the ketone at the 4 position on levulinic acid can be achieved either by chemical catalysis means or by the use of a dehydrogenase biocatalyst. In the context of a metabolic pathway, this last reduction (and corresponding oxidation of one reducing equivalent) ensures the redox balance of the whole pathway from C5 and/or C6 sugars.

In one embodiment of the invention, levulinic acid is separated from the broth or cell-free solution and the ketone at the 4 positions is selectively reduced using homogenous or heterogeneous catalysis to yield 4-hydroxy-pentanoic acid.

In an alternate embodiment of the invention, an NAD(P)-dependent dehydrogenase is used to catalyze the reduction of the ketone at the 4 position on levulinic acid to the corresponding hydroxyl to yield 4-hydroxy-pentanoic acid. In a preferred embodiment, said dehydrogenase reduces the ketone with a high degree of substrate specificity for levulinic acid and high regioselectively for the ketone at the 4 position. Preferably, said dehydrogenase is the same enzyme as for the oxidation of the hydroxyl at the 4 position of 4-oxo-2-hydroxy-pentanoic acid, or a mutant thereof (the mutant being obtained by computational design or experimental mutagenesis, or a combination of the two). In a preferred embodiment of the invention, said dehydrogenase produces selectively one of the enantiomers (4R or 4S) of 4-hydroxy-pentanoic acid. In a alternative embodiment, said dehydrogenase produces a racemic mixture of the 4R and 4S enantiomers of 4-hydroxy-pentanoic acid.

Step 8: Cyclization of 4-hydroxy-pentanoic acid to 4-valerolactone 4-hydroxy-pentanoic acid is cyclized into 4-valerolactone (also known as γ-valerolactone, compound L1 in FIG. 1). In acidic solutions, the thermodynamical equilibrium lies towards the cyclization to 4-valerolactone.

In one embodiment of the invention, 4-valerolactone is produced from 4-hydroxy-pentanoic acid, in the presence of a catalyst, after separation of 4-hydroxy-pentanoic acid from the fermentation broth or cell-free solution. In a preferred embodiment of the invention, an enantiopure 4-hydroxy-pentanoic acid (either the 4R or 4S enantiomer) is converted by said catalyst into the enantiopure 4-valerolactone. In an alternative embodiment, a racemic mixture of the two enantiomers for 4-hydroxy-pentanoic acid (4R and 4S) is converted by said catalyst into a racemic mixture of 4-valerolactone.

In another embodiment of the invention, the lactonization of 4-hydroxy-pentanoic acid to 4-valerolactone is catalyzed directly by a lipase or esterase or protease or lactonase, or mutants thereof (those mutants being obtained by protein engineering using computational design, directed evolution techniques or rational mutagenesis, or a combination of the three) within a cell or outside of a cell. In a preferred embodiment of the invention, said lipase or esterase or protease or lactonase acts on the enantiopure 4-hydroxy-pentanoic acid substrate to yield an enantiopure 4-valerolactone. In a alternative embodiment, said lipase or esterase of protease or lactonase acts on a racemic mixture of the 4R and 4S enantiomers of 4-hydroxy-pentanoic acid to yield a racemic mixture of the 4R and 4S enantiomer of 4-valeralactone.

EXAMPLES

Examples of Pyruvate Decarboxylases Enzymes

An enzyme of the pyruvate decarboxylase family (EC number EC 4.1.1.1) such as pyruvate decarboxylase enzyme can be used to catalyze the first step of the pathway, the conversion of pyruvate to acetaldehyde. Table 1 below lists examples of such enzymes (along with their source organisms), that have been studied and characterized in the literature, with their accession number for the public database GenBank (NCBI) listed. Homologous enzymes, for instance protein and DNA sequences obtained from the sequences in table 1 (or their reverse translation) using an alignment software such as, but not limited to, Blast, PSI-Blast or HMMER3, and with an alignment e-value<0.1, can also be used.

TABLE 1

| GenBank (protein) Accession Number | Organism |
|---|---|
| CAA39398 | Saccharomyces Cerevisiae |
| AAM21208 | Acetobacter pasteurianus |
| NP_195033 | Arabidopsis thaliana |
| AAA20440 | Aspergillus parasiticus |
| EEQ44875 | Candida albicans |
| AAN77243 | Candida glabrata |
| XP_002549529 | Candida tropicalis |
| XP_001703530 | Chlamydomonas reinhardtii |
| AAZ05069 | Citrus Sinensis |

TABLE 1-continued

| GenBank (protein) Accession Number | Organism |
|---|---|
| ADZ22807 | Clostridium acetobytulicun |
| YP_003531827 | Erwinia amylovora |
| AAG13131 | Fragaria x ananassa |
| AAA85103 | Hanseniaspora uvarum |
| CAA59953 | Kluyveromyces lactis |
| AAA35267 | Kluyveromyces marxianus |
| AAP75899 | Lachancea kluyveri |
| AAS49166 | Lactococcus lactis |
| AAA33567 | Neurospora crassa |
| BAC20138 | Oryza sativa |
| AAX33300 (1) and AAX33299 | Petunia x hybrida |
| BAI23188 | Pichia jadinii |
| CAA91444 | Pisum sativum |
| ABU96175 | Populus tremula x Populus alba |
| ABZ79223 | Prunus armeniaca |
| AAM73539 (A) and AAM73540 (B) | Rhizopus oryzae |
| ACM04215 | Rhodobacter sphaeroides |
| NP_948455 | Rhodopseudomonas palustris |
| AAL18557 | Sarcina ventriculi |
| AAC03164 (1) and AAC03165 (2) | Scheffersomyces stipitis |
| CAA90807 | Schizosaccharomyces pombe |
| BAC23043 | Solanum tuberosum |
| AAG22488 | Vitis vinifera |
| CAH56494 | Wickerhamomyces anomalus |
| CAG80835 | Yarrowia lipolytica |
| NP_001105645 | Zea mays |
| CAB65554 | Zygosaccharomyces bisporus |
| AAM49566 | Zymobacter palmae |
| CAA42157 | Zymomonas mobilis |

Examples of Aldolase Enzymes Catalyzing the Production of 4-Hydroxy-2-Keto-Pentanoic Acid:

Homologous enzymes, for instance protein and DNA sequences obtained from the sequences in tables below (or their reverse translation) using an alignment software such as, but not limited to, Blast, PSI-Blast or HMMER3, and with an alignment e-value<0.1, can also be used.

TABLE 2 class I aldolase: EC 4.1.3.39 official name: 4-hydroxy-2-oxovalerate aldolase

| GenBank (protein) Accession Number | Organism |
|---|---|
| P51020 | Escherichia Coli |

TABLE 3 class II aldolases: EC 4.1.3.39 official name: 4-hydroxy-2-oxovalerate aldolase

| GenBank (protein) Accession Number | Organism |
|---|---|
| ADA63518 | Pseudomonas putida |
| ABE37049 | Burkholderia Xenovorans |

TABLE 4 examples of additional pyruvate aldolases susceptible to catalyze the reaction, either as WT or after protein engineering:

| GenBank (protein) Accession Number | EC number | Name | Organism |
|---|---|---|---|
| Q79EM8 | 4.1.2.34 | 4-(2-carboxyphenyl)-2-oxobut-3-enoate aldolase | Nocardioides sp. |

TABLE 4-continued examples of additional pyruvate aldolases susceptible to catalyze the reaction, either as WT or after protein engineering:

| GenBank (protein) Accession Number | EC number | Name | Organism |
| --- | --- | --- | --- |
| Q51947 | 4.1.2.45 | Trans-o-hydroxybenzylidenepyruvate hydratase-aldolase | Pseudomonas Putida |
| NP_746573 | 4.1.3.17 | 4-hydroxy-4-methyl-2-oxoglutarate aldolase | Pseudomonas Putida |

Examples of Dehydrogenase Enzymes Able to Reduce the Ketone at Position 4 of Pentanoic Acid Derivatives to a Secondary Alcohol (Hydroxyl)/Oxidize a Secondary Alcohol (Hydroxyl) at Position 4 of Pentanoic Acid Derivatives to a Ketone:

Homologous enzymes, for instance protein and DNA sequences obtained from the sequences in tables below (or their reverse translation) using an alignment software such as, but not limited to, Blast, PSI-Blast or HMMER3, and with an alignment e-value<0.1, can also be used.

A wide variety of dehydrogenases are capable of oxidizing/reducing secondary alcohols/ketons, with various degrees of substrate specificity. The dehydrogenase sequences listed below areas some examples of dehydrogenases reported in the literature to be active on secondary alcohols/ketones substituents on alkyl chains of three carbons or more.

TABLE 5

| GenBank (protein) Accession Number | EC number | Name | Organism |
| --- | --- | --- | --- |
| CAA09258 | 1.1.1.1 | Medium-chain and short-chain secondary alcohol dehydrogenase | Sulfolobus solfataricus |
| CAA99098 | 1.1.1.B3 * | (S)-specific secondary alcohol dehydrogenase | Saccharomyces cerevisiae |
| AAA34408 | 1.1.1.B4 * | (R)-specific secondary alcohol dehydrogenase | Saccharomyces cerevisiae |
| Q56840 | 1.1.1.268 | 2-(R)-hydroxypropyl-CoM dehydrogenase | Xanthobacter autotrophicus |
| Q56841 | 1.1.1.269 | 2-(S)-hydroxypropyl-CoM dehydrogenase | Xanthobacter autotrophicus |
| ADX68565 | 1.1.1.211 | long-chain-3-hydroxyacyl-CoA dehydrogenase | Weeksella virosa |
| AAK18167 | 1.1.1.35 | 3-hydroxyacyl-CoA dehydrogenase | Pseudomonas putida |
| YP_004366917 | 1.1.1.178 | 3-hydroxy-2-methylbutyryl-CoA dehydrogenase | Marinithermus hydrothermalis |
| NP_062043 | 1.1.1.184 | carbonyl reductase | Rattus norvegicus |

* temporary (non-official) EC numbers assigned by enzyme database BRENDA

Examples of Dehydrogenase Enzymes to Reduce 2,4-Dioxo Pentanoic Acid to 4-Oxo-2-Hydroxy-Pentanoic Acid:

Homologous enzymes, for instance protein and DNA sequences obtained from the sequences in tables below (or their reverse translation) using an alignment software such as, but not limited to, Blast, PSI-Blast or HMMER3, and with an alignment e-value<0.1, can also be used.

Lactate dehydrogenase enzymes with broad substrate specificity demonstrated in the literature to accept the substrate 2,4-dioxo pentanoic acid. The two sequences below have different stereoselectivities.

TABLE 6

| GenBank (protein) Accession Number | EC number | Name | Organism |
| --- | --- | --- | --- |
| 2LDB_A | 1.1.1.27 | L-Lactacte dehydrogenase | Bacillus Stearothermophilus |
| Q5HLAO | 1.1.1.28 | D-Lactate dehydrogenase | Staphylococcus epidermidis |

Example of Dehydratase Enzymes Catalyzing the Conversion of 4-Oxo-2-Hydroxy-Pentanoic Acid to 4-Oxo-2-Pentenoic Acid:

Homologous enzymes, for instance protein and DNA sequences obtained from the sequences in tables below (or their reverse translation) using an alignment software such as, but not limited to, Blast, PSI-Blast or HMMER3, and with an alignment e-value<0.1, can also be used.

Dehydratases of the Enolate Superfamily:

These dehydratase enzymes, which are structurally related to the "enolase" family of enzymes, stabilize the enolate ion formed after abstraction of one of the hydrogen α to the acid functional group. Because these enzymes rely on the stabilization of the enolate anion to decrease the activation energy for the dehydration reaction, they can be active on substrate with the hydroxyl to be eliminated β with either a carboxylic acid, ketone or ester functional groups. Several examples of this class of dehydratase is provided in the table below:

TABLE 7

| GenBank (protein) Accession Number | EC number | Name | Organism |
|---|---|---|---|
| 2HXT_A | 4.2.1.68 | L-fuconate dehdyratase | Xanthomonas Campestris |
| ACT44736 | 4.2.1.32 | L-tartrate dehydratase | Escherichia Coli |
| 2DW7_A | 4.2.1.81 | D-tartrate dehydratase | Bradyrhizobium Japonicum |
| 2I5Q_A | 4.2.1.90 | L-rhamnonate dehydratase | Escherichia Coli |
| YP_003470410 | 4.2.1.39 | gluconate dehydratase | Staphylococcus lugdunensis |
| YP_001461084 | 4.2.1.8 | D-mannonate dehydratase | Escherichia Coli |
| EGP22937 | 4.2.1.6 | D-galactonate dehydratase | Escherichia Coli |

Dehydratases of the Enoyl-coA Hydratase, or "Crotonase", Family:

These enzymes can catalyze the reversible addition/elimination of a water molecule to/from a α,β unsaturated thioesters (coenzyme A derivatives). Because they rely on stabilization of the enolate anion formed after proton abstraction, the enzymes are also able to catalyze the hydration (and reversible dehydration) of α,β unsaturated carboxylic acids and ketones. Contrary to the dehydratase from the enolase superfamily, these enzymes do not require any cofactor.

TABLE 8

| GenBank (protein) Accession Number | EC number | Name | Organism |
|---|---|---|---|
| EGI23865 | 4.2.1.55 | 3-hydroxybinyryl-CoA dehydratase | Escherichia Coli |
| YP_001730392 | 4.2.1.17 | enoyl-CoA hydratase | Escherichia Coli |
| 1DUB_A | 4.2.1.74 | Long-chain enoyl-CoA hydratase | Rattus Norvegicus |
| YP_003022613 | 4.2.1.100 | cyclohexa-1,5-dienecarbonyl-CoA hydratase | Geobacter sp. M21 |
| ACL95949 | 4.2.1.101 | trans-feruloyl-CoA hydratase | Caulobacter Crescentus |
| YP_003394145 | 4.2.1.107 | 3alpha,7alpha,12alpha-trihydroxy-5beta-cholest-24-enoyl-CoA hydratase | Conexibacter woesei |
| AEE35803 | 4.2.1.119 | enoyl-CoA hydratase 2 | Arabidopsis thaliana |

Dehydratases of the Fumarase C Family (Enzymes of the Family Fumarase A and B Use an Iron-Sulfur Cluster):

As for the enoyl-coA hydratases family, these enzymes stabilize the enolate without requiring any cofactor. Substrate binding and transition state stabilization is achieved with active site amino-acids.

TABLE 9

| GenBank (protein) Accession Number | EC number | Name | Organism |
|---|---|---|---|
| ACI83235 | 4.2.1.2 | fumarate hydratase | Escherichia Coli |

Other Dehydratases:

All other known dehydratases (EC numbers 4.2.1.*) may also be used to catalyze the dehydration of 4-oxo-2-hydroxy pentanoic acid to 4-oxo-2-pentenoic acid, such as a dehydratase enzymes relying on an Iron-Sulfur cluster (e.g. dihydroxy-diol dehydratase, fumarase A and C) or vitamin B12-dependent and SAM-dependent dehydratases such as glycerol and propanediol dehydratase.

Examples of Oxidase/Epimerase Enzymes Capable of Catalyzing the Oxidative Dehydration/Conversion of 2,4-Dihydroxy-Pentanoic Acid to 4-Oxo-2-Pentenoic Acid:

Homologous enzymes, for instance protein and DNA sequences obtained from the sequences in tables below (or their reverse translation) using an alignment software such as, but not limited to, Blast, PSI-Blast or HMMER3, and with an alignment e-value<0.1, can also be used.

TABLE 10

| GenBank (protein) Accession Number | EC number | Name | Organism |
|---|---|---|---|
| ZP_01202902 | 4.2.1.115 | UDP-N-acetylglucosamine 4,6-dehydratase | Flavobacteria bacterium |

Examples of Enzymes Catalyzing the Reduction of 4-Oxo, 2-Hydroxo Pentanoic Acid to Levulinic Acid:

Homologous enzymes, for instance protein and DNA sequences obtained from the sequences in tables below (or their reverse translation) using an alignment software such as, but not limited to, Blast, PSI-Blast or HMMER3, and with an alignment e-value<0.1, can also be used.

The family of enzymes called enoate-reductases, or more informally Old Yellow Enzymes, are NAD(P)H and FMN dependent enzyme catalyzing the reversible reduction of α,β unsaturated thioesters, carboxylic acids and ketones. They exhibit broad substrate specificities and the following sequences have been successfully proved experimentally (see data) to catalyze the reduction of 4-oxo, 3-hydroxy pentanoic acid to levulinic acid.

TABLE 11

| GenBank (protein) Accession Number | EC number | Name | Organism |
|---|---|---|---|
| AAA64522 | 1.3.1.31 | Old Yellow Enzyme 1 | *Saccharomyces Cerevisiae* |
| AAD16106 | 1.3.1.31 | 2-cyclohexen-1-one reductase Ncr | *Pseudomonas syringae* |

Multiple point mutants of the enzyme NCR from *Pseudomonas syringae* have also been shown experimentally to exhibit various catalytic activities toward 4-oxo, 2-hydroxo pentanoic acid as a substrate. These mutants correspond to Y178A, P242Q, D338Y and F315Y in the amino-acid numbering of sequence AAD16106.

Examples of Enzymes Able to Catalyze the Lactonization of 4-Hydroxy Acids into their Corresponding Cyclic Esters (Lactones):

Homologous enzymes, for instance protein and DNA sequences obtained from the sequences in tables below (or their reverse translation) using an alignment software such as, but not limited to, Blast, PSI-Blast or HMMER3, and with an alignment e-value<0.1, can also be used.

Figure 5:
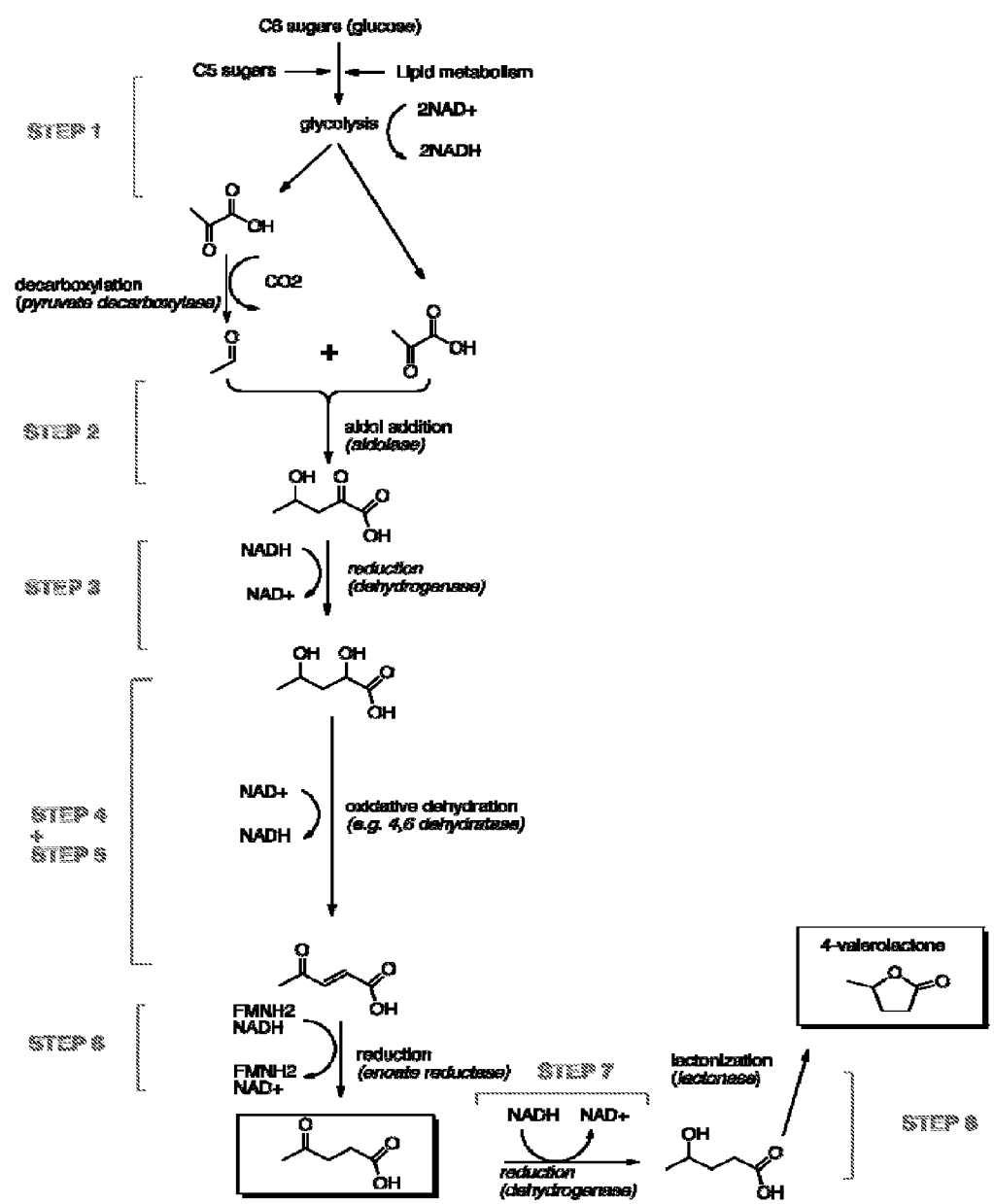
FIG. 5 provides general view of the biochemical pathway/processes of FIG. 3 where step 4 and step 5 are collapsed into one step using an oxidative dehydratase.

Many kinds of lactonases (e.g. lactonohydrolases) are known that can be used to catalyze the reversible formation of 1,4 cyclic esters from 4-hydroxy acids. In particular, 1.4 lactonases (EC 3.1.1.25) show some specificity towards 4-hydroxy acids and are therefore sequences of choice to catalyze the reactions of steps 8 in FIGS. 3, 4 and 5, and the multiple lactonization reactions in FIG. 6. Particularly, some 1,4-lactonases have been assayed with 4-hydroxy pentanoic acid and reported to catalyze its reversible cyclization into gamma-valerolactone. The table below lists some lactonase enzymes that have been reported in the literature to catalyze this reaction.

TABLE 12

| GenBank (protein) Accession Number | EC number | Name | Organism |
|---|---|---|---|
| YP_001903921 | 3.1.1.25 | 1,4 lactonase | *Xanthomonas campestris* |
| AAB41835 | 3.1.1.17 | Paraoxonase 1 (PON1)/ gluconolactonase | *Homo Sapiens* |

A wide variety of other characterized lactonases are susceptible to catalyze the cyclization of 4-hydroxy acids. Below is a table that lists the EC numbers corresponding to existing lactonases (a subclass of carboxyesterases).

TABLE 13

| EC number | Name |
|---|---|
| 3.1.1.15 | *L-arabinolactonase* |
| 3.1.1.17 | *gluconolactonase* |
| 3.1.1.19 | *uronolactonase* |
| 3.1.1.24 | *3-oxoadipate enol-lactonase* |
| 3.1.1.25 | *1,4-lactonase* |
| 3.1.1.27 | *4-pyridoxolactonase* |
| 3.1.1.30 | *D-arabinolactonase* |
| 3.1.1.31 | *6-phosphogluconolactonase* |
| 3.1.1.36 | *limonin-D-ring lactonase* |
| 3.1.1.37 | *steroid-lactonase* |
| 3.1.1.38 | *Triacetate-lactonase* |
| 3.1.1.39 | *actinomycin lactonase* |
| 3.1.1.46 | *deoxylimonate A-ring-lactonase* |
| 3.1.1.57 | *2-pyrone-4,6-dicarboxylate lactonase* |
| 3.1.1.65 | *L-rhamnono-1,4-lactonase* |
| 3.1.1.68 | *xylono-1,4-lactonase* |
| 3.1.1.81 | *quorum-quenching N-acyl-homoserine lactone* |

Finally esterases, lipases and peptidases/amidases have been observed to catalyze lactonization reaction under appropriate experimental conditions (non-alkaline pH and usually room temperature. For example, lipases are referenced in PCT/US2010/055524 for lactonization and amidase/peptidase have been used successfully to synthetize lactones in WO/2009/142489, both of which are hereby incorporated by reference.

Examples of Non-Biocatalytic Methods to Catalyze the Lactonization of 4-Hydroxy Acids into their Corresponding Cyclic Esters (Lactones):

There are multiple non-biocatalytic ways to catalyze the 1,4-lactonization of hydroxacids. For instance, it is well-known that such lactonization is acid-catalyzed and therefore lowering the pH of the medium (whether inside or outside of living cells) increases the rate of the lactonization reaction. Additionally, it has been reported in PCT/US2010/055524 (which is hereby incorporated by reference) that activation through group transfer on the acid functional group of the 4-hydroxy acid is sufficient, under reasonable conditions such as pH 2.5 to 7.0 and room temperature, to yield the lactone form quantitatively. For instance, PCT/US2010/055524 lists (1) activation with a phosphate group (by producing in this case 4-hydroxylbutyryl phosphate) and (2) activation with coenzyme A (by producing 4-hydroxylbutyryl-CoA). Synthesis of the intermediates 4-hydroxylpentanoyl-phosphate or 4-hydroxylpentanoyl-CoA, using a natural or engineered kinase enzyme or CoA synthetase respectively, or chemical synthesis, is expected to result in similar activation and spontaneous lactonization under appropriate conditions.

All references cited herein are hereby incorporated by reference for all purposes.

The invention claimed is:

1. A method for producing 2,4-dihydroxy-pentanoic acid, the method comprising: converting pyruvate to 4 hydroxy-2-oxo-pentanoic acid by aldol addition, and converting 4 hydroxy-2-oxo-pentanoic acid to 2,4-dihydroxy-pentanoic acid through chemical or enzymatic reduction.

2. The method of claim 1, wherein the pyruvate is produced from a carbon source comprising one or more C5 and/or C6 sugars.

3. The method of claim 1, wherein the pyruvate is produced at least in part through glycolysis in a microbial system.

4. The method of claim 3, wherein aldol addition to pyruvate takes place in a eukaryotic, prokaryotic, or archaea fermentation host.

5. The method of claim 4, wherein 4 hydroxy-2-oxo-pentanoic acid is recovered from the fermentation host and converted to 2,4-dihydroxy-pentanoic acid in a cell free system.

6. The method of claim 1, wherein 4-hydroxy-2-oxopentanoic acid is produced from pyruvate by the aldol addition of acetylaldehyde.

7. The method of claim 1 wherein the 2,4-dihydroxypentanoic acid is oxidized to 2-hydroxy 4-oxo pentanoic acid.

8. The method of claim 7, wherein the 2-hydroxy 4-oxo pentanoic acid is converted by dehydratase reaction to 4-oxo-2-pentenoic acid.

9. The method of claim 8, wherein the 4-oxo-2-pentenoic acid is reduced to levulinic acid.

10. The method of claim 9, wherein the levulinic acid is reduced to 4-hydroxy pentanoic acid.

11. The method of claim 10, wherein the 4-hydroxy pentanoic acid is cyclized to 4-valerolactone.

12. The method of claim 1, wherein the 2,4-dihydroxypentanoic acid is converted by oxidative dehydration to 4-oxo-2-pentenoic acid.

13. The method of claim 12, wherein the 4-oxo-2-pentenoic acid is reduced to levulinic acid.

14. The method of claim 13, wherein the levulinic acid is reduced to 4-hydroxy pentanoic acid.

15. The method of claim 14, wherein the 4-hydroxy pentanoic acid is cyclized to 4-valerolactone.

16. The method of claim 6, wherein the acetylaldehyde is prepared by decarboxylation of pyruvate in a microbial host.

17. The method of claim 1, wherein the aldol addition is by a class I or class II aldolase.

18. The method of claim 8, wherein the levulinic acid is converted to 1,4 pentanediol or diphenolic acid, which may optionally be polymerized or co-polymerized with other polymer building blocks.

19. The method of claim 8, wherein the levulinic acid is converted to methyltetrahydrofuran or δ-aminolevulinic acid, which may optionally be incorporated into an herbicide composition.

20. The method of claim 8, wherein the levulinic acid is further polymerized, optionally as a co-polymer with other polymeric building blocks.

21. The method of claim 8, wherein the levulinic acid is converted to a ketal to be used as fuel additive or monomer/co-polymer for the production of plastics and other polymers.

22. A method for producing a polymeric material or polymer-containing product, comprising the method of claim 20.

23. The method of claim 1, wherein the 2,4-dihydroxypentanoic acid is cyclized to 2-hydroxy-4-valerolactone.

24. The method of claim 1, wherein the 2,4-dihydroxypentanoic acid is converted to 2,4-dihydroxy-pentanoyl-CoA via CoA attachment.

25. The method of claim 24, wherein the 2,4-dihydroxy-pentanoyl-CoA is oxidized to 2-hydroxy-4-oxo-pentanoyl-CoA.

26. The method of claim 7, wherein the 2-hydroxy 4-oxo pentanoic acid is converted to 2-hydroxy-4-oxo pentanoyl-CoA via CoA attachment.

27. The method of claim 8, wherein the 4-oxo-2-pentenoic acid is reduced to 4-hydroxy-2-pentenoic acid.

28. The method of claim 1, wherein the 2,4-dihydroxypentanoic acid is converted to angelica lactone.

* * * * *